US008551467B2

(12) United States Patent
Sullivan et al.

(10) Patent No.: US 8,551,467 B2
(45) Date of Patent: Oct. 8, 2013

(54) REPLENISHMENT AND ENRICHMENT OF OCULAR SURFACE LUBRICATION

(75) Inventors: Benjamin Sullivan, San Diego, CA (US); Tannin A. Schmidt, Calbary, CA (US); David A. Sullivan, Boston, MA (US)

(73) Assignees: The Regents of the University of California, Oakland, CA (US); Schepens Eye Research Institute, Boston, MA (US)

( * ) Notice: Subject to any disclaimer, the term of this patent is extended or adjusted under 35 U.S.C. 154(b) by 0 days.

(21) Appl. No.: 13/539,986

(22) Filed: Jul. 2, 2012

(65) Prior Publication Data

US 2012/0321611 A1 Dec. 20, 2012

Related U.S. Application Data

(60) Division of application No. 12/605,024, filed on Oct. 23, 2009, which is a continuation of application No. PCT/US2009/039887, filed on Apr. 8, 2009.

(60) Provisional application No. 61/051,112, filed on May 7, 2008.

(51) Int. Cl.
*C12N 9/50* (2006.01)
*A61K 38/48* (2006.01)

(52) U.S. Cl.
USPC .............. 424/78.04; 424/94.63; 435/219; 514/20.8

(58) Field of Classification Search
USPC .......... 424/78.04, 94.63; 435/219; 514/20.8
See application file for complete search history.

(56) References Cited

U.S. PATENT DOCUMENTS

| 4,801,619 | A | 1/1989 | Lindblad |
|---|---|---|---|
| 4,964,206 | A | 10/1990 | Knoll |
| 5,286,829 | A | 2/1994 | Fedorov et al. |
| 5,351,100 | A | 9/1994 | Schwenzfeier et al. |
| 5,702,456 | A | 12/1997 | Pienkowski |
| 5,942,558 | A | 8/1999 | Korb |
| 6,107,289 | A | 8/2000 | Sullivan |
| 6,635,267 | B1 | 10/2003 | Miyoshi et al. |
| 6,689,748 | B1 | 2/2004 | Theoharides |
| 6,815,074 | B2 | 11/2004 | Aguado et al. |
| 6,940,580 | B2 | 9/2005 | Winterton et al. |
| 7,014,860 | B1 | 3/2006 | Kawata et al. |
| 7,329,415 | B2 | 2/2008 | Lally et al. |
| 7,811,267 | B2 | 10/2010 | Norrby et al. |
| 2003/0008154 | A1 | 1/2003 | Aguado et al. |
| 2003/0130324 | A1 | 7/2003 | Mcavoy et al. |
| 2003/0219909 | A1 | 11/2003 | Lally et al. |
| 2004/0009893 | A1 | 1/2004 | Wang et al. |
| 2004/0029913 | A1 | 2/2004 | Dalton et al. |
| 2004/0157073 | A1 | 8/2004 | Burrell et al. |
| 2005/0063996 | A1 | 3/2005 | Peyman |
| 2005/0129778 | A1 | 6/2005 | Mulye |
| 2005/0196370 | A1 | 9/2005 | Yu et al. |
| 2005/0287223 | A1 | 12/2005 | Peyman |
| 2006/0067927 | A1 | 3/2006 | Chandrasekaran et al. |
| 2006/0228394 | A1 | 10/2006 | Peyman |
| 2006/0281739 | A1 | 12/2006 | Gadek et al. |
| 2007/0031471 | A1 | 2/2007 | Peyman |
| 2007/0191268 | A1 | 8/2007 | Flannery et al. |
| 2007/0249557 | A1 | 10/2007 | Jay |
| 2007/0264226 | A1 | 11/2007 | Karagoezian et al. |
| 2007/0275032 | A1 | 11/2007 | Wimmer et al. |
| 2007/0292496 | A1 | 12/2007 | Herrero Vanrell et al. |
| 2008/0053845 | A1 | 3/2008 | Newman |
| 2008/0076829 | A1 | 3/2008 | Dalton et al. |
| 2008/0094573 | A1 | 4/2008 | Vermette et al. |
| 2008/0097606 | A1 | 4/2008 | Cragg et al. |
| 2008/0197324 | A1 | 8/2008 | Zhao et al. |
| 2008/0213274 | A1 | 9/2008 | Sabbadini et al. |
| 2009/0060933 | A1 | 3/2009 | Estell et al. |
| 2009/0068247 | A1 | 3/2009 | Jay |
| 2009/0160074 | A1 | 6/2009 | Pruitt et al. |
| 2011/0070222 | A1 | 3/2011 | Sullivan et al. |
| 2011/0142908 | A1 | 6/2011 | Sullivan et al. |

FOREIGN PATENT DOCUMENTS

| WO | 94/06485 A1 | 3/1994 |
|---|---|---|
| WO | 00/27421 A2 | 5/2000 |
| WO | 03030941 | 4/2003 |
| WO | 03/057270 A1 | 7/2003 |
| WO | 03057270 | 7/2003 |
| WO | 2004/035736 A2 | 4/2004 |
| WO | 2005016130 | 2/2005 |
| WO | 2005027933 | 3/2005 |
| WO | 2005110473 | 11/2005 |
| WO | 2006/094026 A1 | 9/2006 |

OTHER PUBLICATIONS

U.S. Appl. No. 12/940,370.*
International Search Report for PCT/US2010/53797 dated Jan. 6, 2011 (1 page).
International Search Report for PCT/US2009/039887 dated Aug. 24, 2009 (1 page).
Jay et al., 2010, "Prevention of Cartilage Degeneration and Restoration of Chondroprotection by Lubricin Tribosupplementation in the Rat Following Anterior Cruciate Ligament Transection," Arthritis & Rheumatism, 62 (8):2382-2391.

(Continued)

*Primary Examiner* — Ruth Davis
(74) *Attorney, Agent, or Firm* — Sutherland Asbill & Brennan LLP

(57) ABSTRACT

An ophthalmic composition, and methods of use thereof, including for treating ocular boundary deficiency, symptoms associated therewith, or undesired condition that is associated with or causes ocular boundary deficiency at the ocular surface or for the treatment or care of ophthalmic devices. The ophthalmic composition comprises a human PRG4 protein, a lubricant fragment, homolog, or isoform thereof, suspended in an ophthalmically acceptable balanced salt solution. The ophthalmic composition may also comprise one or more ophthalmically acceptable agents.

17 Claims, 10 Drawing Sheets

(56) References Cited

OTHER PUBLICATIONS

Foulks, 2006, "Pharmacological Management of Dry Eye in the Elderly Patient," Therapy in Practice, 25(2):105-118.

Japanese Office Action dated Nov. 20, 2012 for Japanese Application No. 2011-508534.

Japanese Office Action dated Nov. 20, 2012 for Japanese Application No. 2011-508633.

Japanese Office Action dated Nov. 20, 2012 for Japanese Application No. 2011-508634.

Supplementary European Search Report for EP Application No. 09 74 3204, mailed Jun. 7, 2011, (2 pages).

Written Opinion for PCT/US09/39887, mailed Aug. 24, 2009.

Written Opinion for PCT/US10/53797, mailed Jan. 6, 2011.

Zappone et al. "Adsorption, lubrication, and wear of lubricin on model surfaces: polymer brush-like behavior of a glycoprotein" Biophys J. Mar. 1, 2007;92(5):1693-708.

* cited by examiner

U 5th Min

REPLENISHMENT AND ENRICHMENT OF OCULAR SURFACE LUBRICATION

CROSS-REFERENCE TO RELATED APPLICATIONS

This patent application is a divisional of U.S. application Ser. No. 12/605,024 filed on Oct. 23, 2009, which is a continuation-in-part of PCT Application No. PCT/US09/39887, filed Apr. 8, 2009, which claims priority benefit of U.S. Provisional Application No. 61/051,112 filed May 7, 2008, each of which is incorporated herein by reference in their entireties.

GOVERNMENT SUPPORT

This invention was made with government support under NIH Grant No. EY05612. The government has certain rights in the invention.

FIELD OF THE INVENTION

The present invention relates to the management of ocular lubrication. In particular, the present invention relates to pharmaceutical compositions, and method of use thereof, including for treating diseases associated with compromised lubrication at the corneal and conjunctival surfaces and treating ophthalmic devices.

BACKGROUND

The proteoglycan 4 (prg4) gene encodes for highly glycosylated proteins termed megakaryocyte stimulating factor (MSF), lubricin, and superficial zone protein (SZP) (1)). Lubricin was first isolated from synovial fluid and demonstrated lubricating ability in vitro similar to synovial fluid at a cartilage-glass interface (2). Lubricin was later identified as a product of synovial fibroblasts (3) and also shown to possess boundary lubricating ability at a latex-glass interface by Jay et al. (3-9). O-linked β(1-3)Gal-GalNAc oligosaccharides within a large mucin like domain of 940 amino acids (10), encoded for by exon 6, were subsequently shown to mediate, in part, this boundary lubricating ability (8). SZP was first localized at the surface of explant cartilage from the superficial zone and isolated from conditioned medium (11). SZP also demonstrated lubricating ability at a cartilage-glass interface (12). These molecules are collectively referred to as PRG4. PRG4 was also shown to be present at the surface of synovium (58), tendon (13), and meniscus (14). In addition, PRG4 has been shown to contribute, both at physiological and pathophysiological concentrations, to the boundary lubrication of apposing articular cartilage surfaces (59).

The functional importance of prg4 was shown by mutations that cause the camptodactyly-arthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion (15). Also, in PRG4-null mice, cartilage deterioration and subsequent joint failure were observed (16). Therefore, PRG4 expression is a necessary component of healthy synovial joints.

PRG4 is a member of the mucin family, which are generally abundant on epithelial linings and provide many functions, including lubrication and protection from invading microorganisms (17). The functional properties of mucins are generally determined by specialized glycosylation patterns and their ability to form multimers through intermolecular disulfide bonds (18), both of which are altered in chronic diseases (e.g. cystic fibrosis, asthma) (17). Biochemical characterization of PRG4 isolated from synovial fluid (2, 19) showed molecular heterogeneity in O-glycosylation, which appears to influence lubricating properties (8) Recently, PRG4 from bovine synovial fluid has been shown to exist as disulfide-bonded dimers, in addition to the monomeric forms, as suggested by the conserved cysteine-rich domains at both N- and C-terminals, along with an unpaired cysteine at the C-terminal (20).

In tissues such as synovial joints, physicochemical modes of lubrication have been classified as fluid film or boundary. The operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, the interstitial fluid within cartilage becomes pressurized, due to the biphasic nature of the tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a very low $\mu$. Also, at the onset of loading and/or motion, squeeze film, hydrodynamic, and elastohydrodynamic types of fluid film lubrication occur, with pressurization, motion, and deformation acting to drive viscous lubricant from and/or through the gap between two surfaces in relative motion.

The relevant extent to which fluid pressure/film versus boundary lubrication occurs classically depends on a number of factors (31). When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. A boundary mode of lubrication is therefore indicated by a friction coefficient (ratio of the measured frictional force between two contacting surfaces in relative motion to the applied normal force) during steady sliding being invariant with factors that influence formation of a fluid film, such as relative sliding velocity and axial load (35). For articular cartilage, it has been concluded boundary lubrication is certain to occur, although complemented by fluid pressurization and other mechanisms (36-39).

In boundary lubrication, load is supported by surface-to-surface contact, and the associated frictional properties are determined by lubricant surface molecules. This mode has been proposed to be important because the opposing cartilage layers make contact over ~10% of the total area, and this may be where most of the friction occurs (30). Furthermore, with increasing loading time and dissipation of hydrostatic pressure, lubricant-coated surfaces bear an increasingly higher portion of the load relative to pressurized fluid, and consequently, this mode can become increasingly dominant (31, 32). Boundary lubrication, in essence, mitigates stick-slip (31), and is therefore manifest as decreased resistance both to steady motion and the start-up of motion. The latter situation is relevant to load bearing articulating surfaces after prolonged compressive loading (e.g., sitting or standing in vivo) (33). Typical wear patterns of cartilage surfaces (34) also suggest that boundary lubrication of articular cartilage is critical to the protection and maintenance of the articular surface structure.

With increasing loading time and dissipation of hydrostatic pressure, lubricant-coated surfaces bear an increasingly higher portion of the load relative to pressurized fluid, and consequently, μ can become increasingly dominated by this mode of lubrication. A boundary mode of lubrication is indicated by values of μ during steady sliding being invariant with factors that influence formation of a fluid film, such as relative sliding velocity and axial load. Boundary lubrication, in essence, mitigates stickslip, and is therefore manifest as decreased resistance both to steady motion and the start-up of motion.

The accumulation of PRG4 within synovial fluid and at the articular surface, are likely key functional determinants of PRG4's boundary lubricating ability. Recently, it was demonstrated that a significant, threefold secretion of PRG4 resulted from the dynamic shear loading of cultured cartilage explants, as compared to free-swelling or statically compressed cultures (27). This PRG4 synthesis and secretion by chondrocytes could significantly contribute to the concentration of PRG4 within synovial fluid, in both homeostatic and pathological conditions where physiological regulators are present (23). Although the amount of PRG4 bound to the surface does not appear to correlate with secretion rates, previous studies suggest surface bound PRG4 can exchange with endogenous PRG4 in synovial fluid (25), especially under the influence of mechanical perturbation (26, 27). Clarification of the spatial and temporal aspects of PRG4 metabolism within the joint, particularly at the articular surface, would further the understanding of PRG4's contribution to the low-friction properties of articular cartilage, and possibly lead to treatments to prevent loss of this function (40, 41). More remains to be determined about the processing, and the potentially additional or alternative functions of various PRG4 molecules of different molecular weight (10, 27, 28, 61). Moreover, the combination of chemical and mechanical factors to stimulate PRG4 expression in chondrocytes near the articular surface may be useful for creating tissue engineered cartilage from isolated sub-populations (29) with a surface that is bioactive and functional in lubrication.

The precise mechanisms of boundary lubrication at biological interfaces are currently unknown. However, proteoglycan 4 (PRG4) may play a critical role as a boundary lubricant in articulating joints. This secreted glycoprotein is thought to protect cartilaginous surfaces against frictional forces, cell adhesion and protein deposition. Various native and recombinant lubricin proteins and isoforms have been isolated and characterized. For instance, U.S. Pat. Nos. 5,326,558; 6,433,142; 7,030,223, and 7,361,738 disclose a family of human megakaryocyte stimulating factors (MSFs) and pharmaceutical compositions containing one or more such MSFs for treating disease states or disorders, such as a deficiency of platelets. U.S. Pat. Nos. 6,960,562 and 6,743,774 also disclose a lubricating polypeptide, tribonectin, comprising a substantially pure fragments of MSF, and methods of lubricating joints or other tissues by administering tribonectin systemically or directly to tissues.

SUMMARY OF THE INVENTION

The present invention provides, in various embodiments, pharmaceutical compositions, and methods of use thereof, for managing ocular lubrication, including the therapeutic replenishment and enrichment of boundary lubricant molecules at the ocular surface. Described in certain embodiments of the present invention is the observation that PRG4 mRNA is expressed in human corneal and conjunctival epithelial cells, as well as in mouse lacrimal and meibomian glands, indicating that PRG4 protein is presented in these tissues on the ocular surface. Described in certain instances of the present invention is the observation that the role PRG4 protein serves on the ocular surface is to protect the cornea and conjunctiva against significant shear forces generated during an eyelid blink, contact lens wear, and other undesirable conditions. The impact of the tear film, including the impact of inflammation, proinflammatory cytokines, sex steroid imbalance and proteases on the composition and function of the films, suggest a course of therapy for ocular tissues which promotes boundary lubrication.

In certain embodiments, the present invention provides a pharmaceutical composition suitable for topical application to an ocular surface comprising a therapeutically effective concentration of a PRG4 protein suspended in an ophthalmically acceptable balanced salt solution. The pharmaceutical composition of the present invention may also comprise one or more ophthalmically acceptable agents selected from the group consisting of an ophthalmically acceptable demulcent, ophthalmically acceptable excipient, ophthalmically acceptable astringent, ophthalmically acceptable vasoconstrictor, and ophthalmically acceptable emollient.

Exemplary ophthalmically acceptable demulcents contemplated in the present invention include, but are not limited to, carboxymethylcellulose sodium (e.g., about 0.2 to 2.5% w/v), hydroxyethyl cellulose (e.g., about 0.2 to 2.5% w/v), hypromellose (e.g., about 0.2 to 2.5% w/v), methylcellulose (e.g., about 0.2 to 2.5% w/v), dextran 70 (e.g., about 0.1% w/v), gelatin (e.g., about 0.01% w/v), glycerin (e.g., about 0.2 to 1% w/v), polyethylene glycol 300 (e.g., about 0.2 to 1% w/v), polyethylene glycol 400 (e.g., about 0.2 to 1% w/v), polysorbate 80 (e.g., about 0.2 to 1% w/v), propylene glycol (e.g., about 0.2 to 1% w/v), polyvinyl alcohol (e.g., about 0.1 to 4% w/v), povidone (e.g., about 0.1 to 2% w/v). Exemplary ophthalmically acceptable excipients/emollients contemplated in the present invention include, but are not limited to, anhydrous lanolin (e.g., about 1 to 10% w/v), lanolin (e.g., about 1 to 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v). An exemplary ophthalmically acceptable astringent contemplated in the present invention includes, but is not limited to, zinc sulfate (e.g., about 0.25% w/v). Exemplary ophthalmically acceptable vasoconstrictors contemplated in the present invention include, but are not limited to, ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v).

In some of these embodiments, the demulcents, excipients, astringents, vasoconstrictors, emollients and electrolytes provide a means to deliver the PRG4 protein in an ophthalmically acceptable manner. Ophthalmically acceptable compositions are suitable for topical application to the ocular surface if they lack unacceptable eye toxicity, burning, itchiness, viscosity, blurred vision, etc. upon application.

In certain embodiments, the pharmaceutical composition of the present invention further comprises a therapeutically effective concentration of one or more additional therapeutic agents, including but not limited to, sodium hyaluronate, hyaluronic acid, and phospholipid. Exemplary phospholipid includes, but is not limited to, L-α-dipalmitoylphosphatidylcholine, phosphatidylcholine, phosphatidylethanolamine and sphingomyelin.

In certain embodiments, the present invention provides a pharmaceutical composition suitable for topical application to an ocular surface comprising a therapeutically effective concentration of PRG4 protein suspended in an ophthalmically acceptable balanced salt solution comprising at least three electrolytes, including but not limited to, sodium chloride (NaCl) 0.64%, potassium chloride (KCl) 0.075%, calcium chloride dihydrate (CaCl2.2H2O) 0.048%, magnesium chloride hexahydrate (MgCl2.6H2O) 0.03%, sodium acetate trihydrate (C2H3NaO2.3H2O) 0.39%, sodium citrate dehydrate (C6H5Na3O7.2H2O) 0.17%, sodium hydroxide and/or hydrochloric acid (to adjust pH to approximately 7.5) with an osmolarity of approximately 300 mOsms/L.

In certain embodiments, the present invention provides a pharmaceutical composition suitable for topical application to an ocular surface comprising a therapeutically effective concentration of PRG4 protein suspended in an ophthalmically acceptable balanced salt solution, comprised of sodium (Na+) of approximately 128 mM, potassium (K+) of approximately 24 mM, chloride (Cl−) of approximately 113 mM, calcium (Ca2+) of approximately 0.4 mM, magnesium (Mg2+) of approximately 0.3 mM, HCO3- of approximately 5 mM, citrate of approximately 1 mM, phosphate of approximately 14 mM, acetate of approximately 15 mM, and sodium hydroxide and/or hydrochloric acid (to adjust pH to approximately 7.5) with an osmolarity of approximately 300 mOsms/L.

The present invention further provides a method for treating ocular lubrication deficiency, or symptoms associated therewith, in an individual in need. The method comprises topically administering to the ocular surface of the individual in need a pharmaceutical composition comprising a therapeutically effective concentration of a PRG4 protein. In certain embodiments, the pharmaceutical composition comprising the PRG4 protein is administered in combination with an ophthalmically acceptable formulation comprising one or more ophthalmically acceptable agents selected from the group consisting of an ophthalmically acceptable demulcent, ophthalmically acceptable excipient, ophthalmically acceptable astringent, ophthalmically acceptable vasoconstrictor, and ophthalmically acceptable emollient.

In some embodiments, the pharmaceutical composition comprising the PRG4 protein is administered in combination with an ophthalmically acceptable solution comprising a therapeutically effective concentration of sodium hyaluronate or hyaluronic acid, or a surface active phospholipid, as discussed above. In yet certain embodiments, the pharmaceutical composition comprising the PRG4 protein is administered in combination with a phosphate buffered saline solution or an ophthalmically acceptable balanced salt solution comprising one or more electrolytes, as discussed above.

The present invention provides a method for treating a deficiency in ocular lubrication or symptoms associated therewith, that due to tear loss or unstable tear film in the ocular boundary loop, such as androgen deficiency, Sjogren's syndrome and keratoconjunctivitis sicca (KCS). Such method comprises topically administering to the ocular surface of a patient in need the pharmaceutical composition of the present invention.

In certain embodiments, the present invention further provides a method for addressing and treating the conditions associated with unfavorable or deficient ocular lubrication. Exemplary conditions include, but are not limited to aqueous or evaporative dry eye disease, Sjogren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging.

DETAILED DESCRIPTION OF THE INVENTION

Figure 1:
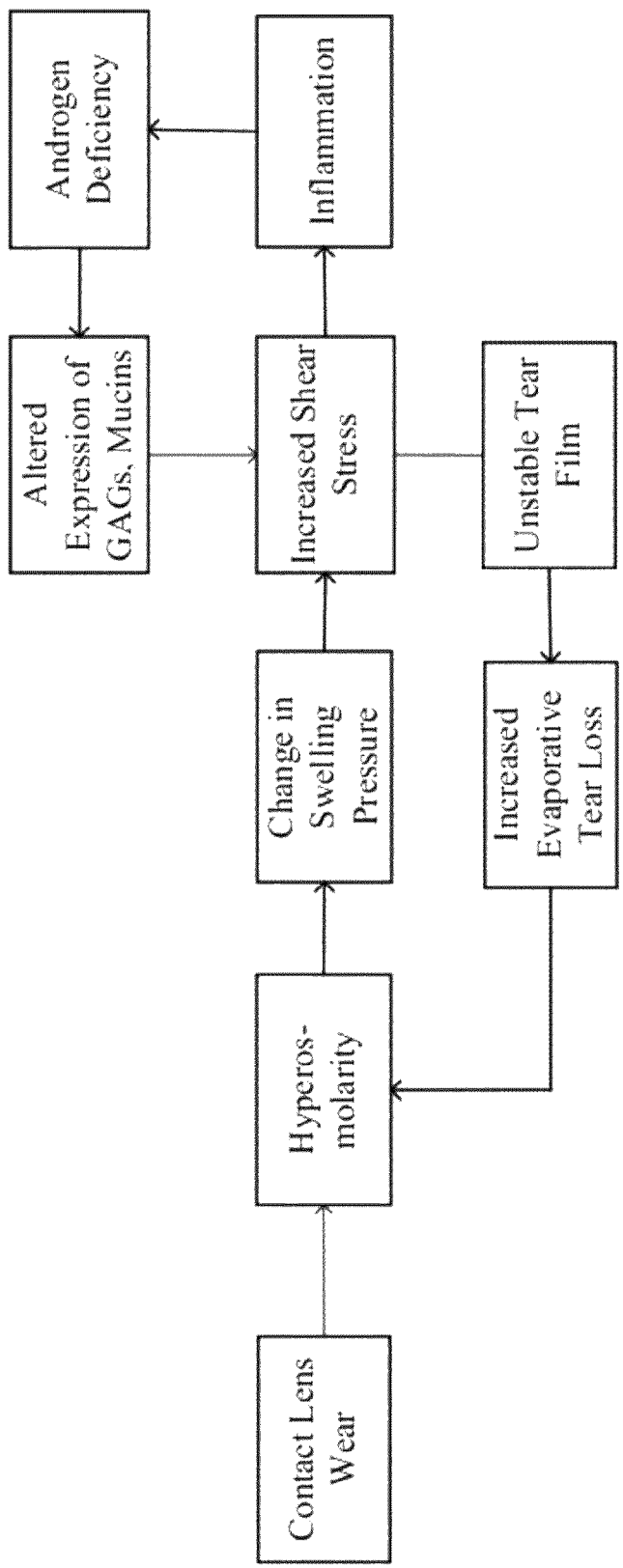
FIG. 1 represents feedback loops within ocular surface boundary lubrication.
Figure 2:
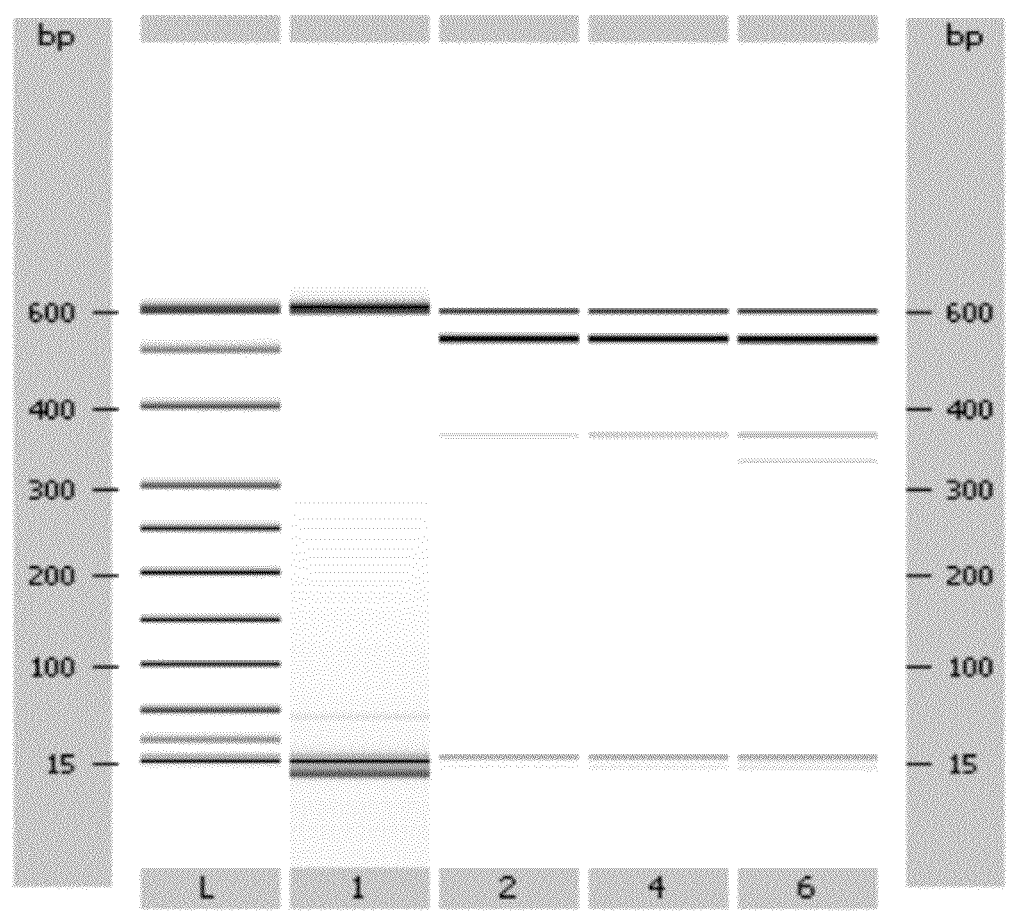
FIG. 2 illustrates PRG4 mRNA expression in human corneal epithelial cells. Human corneal epithelial cells were isolated from the corneoscleral rims of male and female donors. Amplified samples were screened for the presence of PRG4 products by using an Agilent 2100 Bioanalyzer. Vertical lanes contain: L. MW ladder; 1. No template control; 2. Corneal tissue from a 33-year female; 4. Cultured corneal epithelial cells from a 70-year female; 6. Cultured corneal epithelial cells from a 53-year male.
Figure 3:
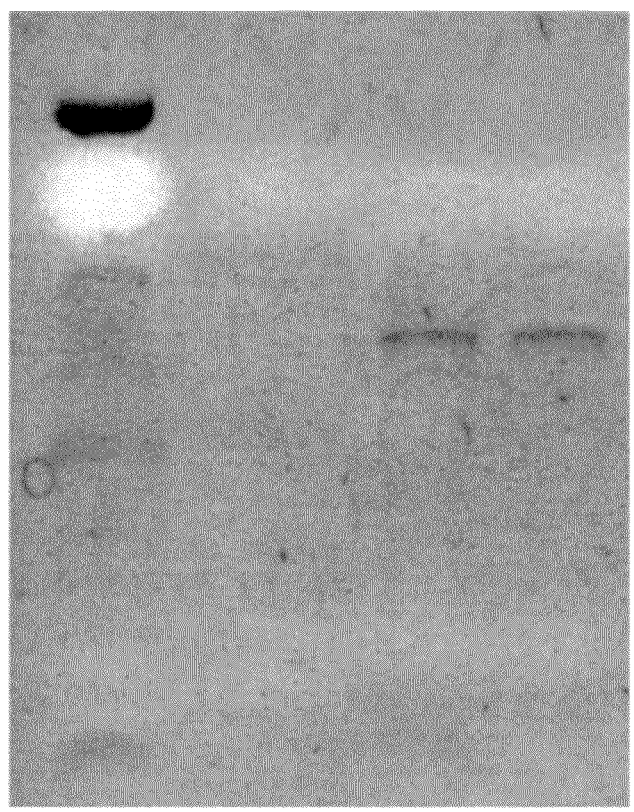
FIG. 3 illustrates PRG4 mRNA expression in human conjunctival epithelial cells. Human corneal epithelial cells were isolated from the corneoscleral rims of male and female donors. Amplified samples were screened for the presence of PRG4 products by using agarose gel electrophoresis. Vertical lanes contain: 1. MW ladder; 2. No template control; 4. Human female conjunctiva; 5. Human male conjunctiva.
Figure 4:
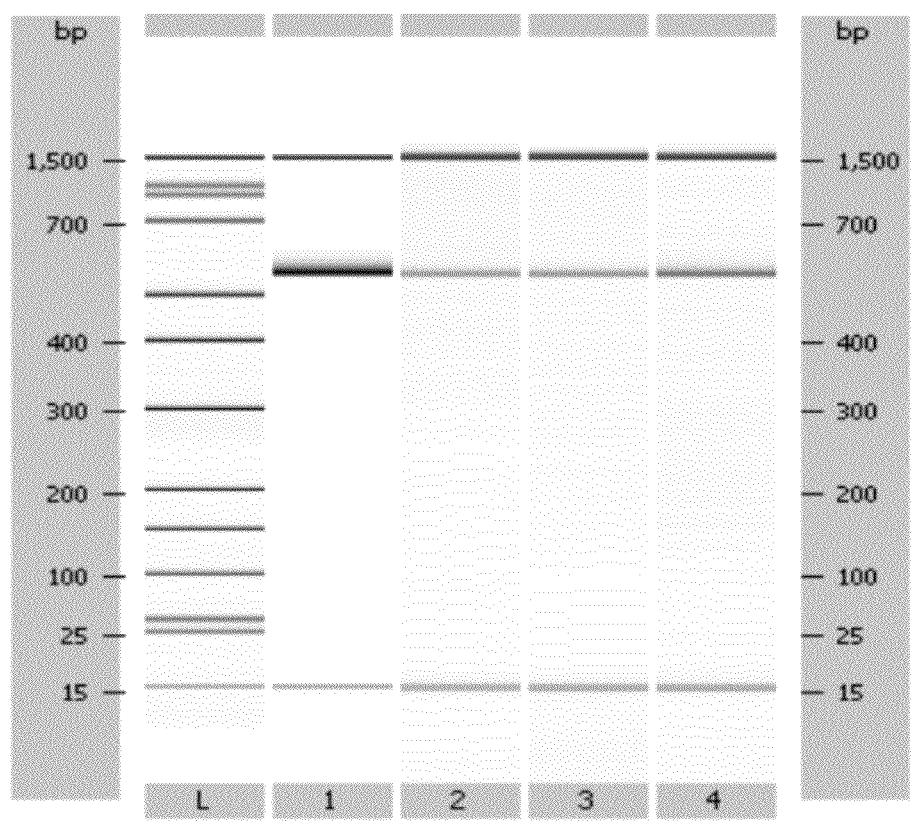
FIG. 4 illustrates PRG4 mRNA expression in human corneoscleral rim tissue samples. L. Human corneal epithelial cells were isolated from the corneoscleral rims of male and female donors. Amplified samples were screened for the presence of PRG4 products by using an Agilent 2100 Bioanalyzer. Vertical lanes contain: MW ladder; 1. Human liver cDNA standard; 2. Corneoscleral rim tissue from a 24-year female; 3. Corneoscleral rim tissue from a 51-year female; 4. Human conjunctival epithelial cells.
Figure 5:
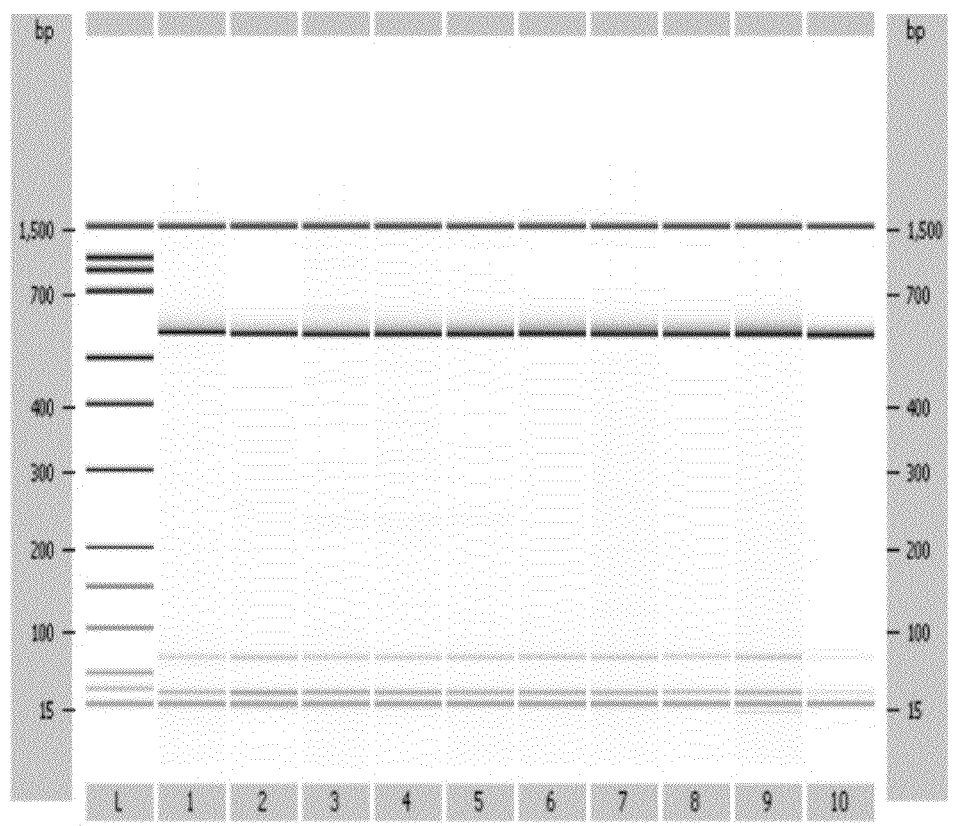
FIG. 5 illustrates PRG4 mRNA expression in human conjunctival impression cytology samples. Conjunctival impression cytology samples were isolated from male and female donors. Amplified samples were screened for the presence of PRG4 products by using an Agilent 2100 Bioanalyzer. Vertical lanes contain: L. MW ladder; 1-9. Conjunctival impression cytology samples; 10. Repeat of human conjunctival epithelial cells (Lane 4 in FIG. 3).

Provided in certain embodiments herein, is a method for treating ocular lubrication deficiency (e.g., ocular boundary lubrication deficiency), or symptoms associated therewith, in an individual in need thereof comprising topically administering to the ocular surface of the individual a pharmaceutical composition comprising a therapeutically effective amount of PRG4 protein. Also provided in some embodiments herein are pharmaceutical compositions comprising PRG4 protein in an ophthalmically acceptable formulation. In specific embodiments, provided herein is a pharmaceutical composition suitable for topical application to an ocular surface comprising a therapeutically effective amount of PRG4 suspended in an ophthalmically acceptable balanced salt solution, and may also be in combination with one or more ophthalmically acceptable agents selected from the group consisting of an ophthalmically acceptable demulcent, an ophthalmically acceptable excipient, an ophthalmically acceptable astringent, an ophthalmically acceptable vasoconstrictor, and an ophthalmically acceptable emollient. In some embodiments, the composition is used to treat an ophthalmic device (e.g., contact lens) and administered to the ocular surface with and/or on the surface of the ophthalmic device (e.g., contact lens).

Provided in some embodiments herein are pharmaceutical compositions, and methods of use thereof, for treating a deficiency in ocular lubrication at the ocular surface (e.g., a deficiency of, such as decreased or undesirable, ocular boundary lubrication). A pharmaceutical composition of certain embodiments of the present invention comprises an isolated or purified PRG4 protein suspended in an ophthalmically acceptable balanced salt solution in combination with one or more ophthalmic agents selected from the group consisting of an ophthalmic demulcent, excipient, astringent, vasoconstructor, and emollient. In some embodiments, any pharmaceutical composition provided herein further comprises one or more additional therapeutic agents selected from the group consisting of sodium hyaluronate, surface active phospholipids, and electrolytes in a pharmaceutically acceptable carrier for topical administration.

The present invention provides, in certain embodiments, a novel approach to manage ocular lubrication, including the therapeutic replenishment and enrichment of boundary lubricant molecules at the ocular surface. It should be noted that the importance and the mechanism of ocular boundary lubrication has not heretofore been recognized within the ophthalmic community. For years, the scientific consensus within the orthopaedic research community was that hydrodynamic lubrication was by far the dominant mode of lubrication for articular cartilage, and that boundary lubrication was simply an afterthought. Moreover, those researchers studying boundary lubrication at cartilage surfaces suggest that boundary lubrication is likely only important under "high load and low velocity," which are opposite to the conditions at the ocular surface, where there are relatively low axial loads and relatively fast sliding velocities. See, e.g., (54). Moreover, boundary lubrication involving the corneal glyocalyx has not heretofore been considered. Jay et al. compared purified lubricating factor from bovine synovial fluid to "mucinous glycoprotein from human submandibular saliva and stimulated tears," and concluded "mucin secreted by the lacrimal gland did not lubricate," overlooking the possibility that the corneal epithelium was a source of lubricant or that boundary lubrication was an important contributor at the ocular surface. See, e.g., (55). The most recent mathematical models of tear film dynamics also ignore the possibility of boundary lubrication, claiming a "lubrication approximation" for the height of the tear film such that "the mucus layer on the cornea can be taken to provide a no-slip surface for the aqueous film" and that "it should be noted that the model only predicts the evolution prior to the [tear film] thickness reaching some critically thin value at which the model breaks down." See, e.g., (57).

There is a need to manage ocular lubrication and protect the cornea and conjunctiva against significant shear forces generated from the undesirable conditions described herein, including, by way of non-limiting example, aqueous or evaporative dry eye disease, Sjogren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging.

In some instances, the loading of cornea and conjunctiva is likely dominated by shear forces. In certain instances, eyelid blinking, as well as contact lens wear, generates significant stress upon ocular surface epithelial cells, and this is especially true in the presence of a compromised tear film. As shown in FIG. 1, it is suggested that increased shear stress leads to tear film instability, evaporative tear loss, hyperosmolarity, changes in swelling pressure and a feedback elevation in shear stress. In some instances, increased shear stress is also thought to promote inflammation, androgen deficiency and decreased expression of proteoglycans. In certain instances increased shear stress and its sequelae may, over time, lead to a loss of boundary lubrication at the ocular surface.

A deficiency in ocular lubrication and symptoms associated therewith can be determine by any suitable method. In some instances, a deficiency in ocular lubrication and symptoms associated therewith is defined either qualitatively (e.g., a feeling of low lubrication, dry eye, discomfort, etc.) or quantitatively (e.g., measured through mechanical, biochemical, electrical, optical or other methods of quantitative assays).

In certain instances, in undesirable conditions for ocular boundary lubrication, such those resulting from aqueous or evaporative dry eye disease, Sjogren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging, a compromised tear film will exist. In some of these situations, increased evaporation may preclude efficient fluid film lubrication, but allow boundary lubrication and a molecular sacrificial mechanism to reduce shear stress at the cell surface. Certain embodiments of the present invention provide that therapeutic replenishment and enrichment of boundary lubricant molecules at the ocular surface would interrupt the feedback loop through which the unfavorable conditions associated with a deficiency in ocular lubrication promote ocular surface distress.

In certain instances, and as provided herein, PRG4 protein plays a critical role in the eye as a boundary lubricant. In some instances, this secreted glycoprotein protects the ocular surface to protect the cornea and conjunctiva against significant shear forces generated during an eyelid blink, contact lens wear, and any other undesirable ocular boundary lubrication caused by chronic inflammation and hyperosmolarity that result from dry eye disease, androgen deficiency, estrogen replacement therapy, compromised tear film, allergy, aging, ocular surface diseases, and increased protease levels in the tear film and at the ocular surface. Given the relationship between osmotic pressure and the electromechanical interactions within charged molecules, the present invention provides, in some embodiments, a pharmaceutical composition for managing a deficiency in ocular lubrication by modulating hyperosmolarity or osmolarity at the ocular surface via interrupting the feedback mechanisms that prevent secreted components from reducing friction coefficients and mitigating shear stress.

In another exemplary embodiment, the present invention features a sacrificial mechanism for ocular boundary lubrication, whereby surface bound receptors reversibly bind one or more gel forming or surfactant constructs. In some instances, the gel forming or surfactant constructs detach during a shear event, thereby preventing the shear stress from reaching (or reducing the shear stress reaching) the epithelial surface. In certain embodiments, following the transient shearing event, the gel forming and surfactant constructs, allowed to return to their undisturbed equilibrium, rebind to the surface bound receptors. In some embodiments, the entire construct can detach during shear. One could imagine, in certain instances, that the thermodynamics of this equilibrium would increase the probability of release from the receptor with increasing shear amplitude, but that any one association is easily reversible.

In one embodiment of the current invention, the pharmaceutical composition comprising a PRG4 protein suspended in an ophthalmically acceptable balanced solution is applied topically to the ocular surface, where the PRG4 protein associates or binds to. In certain instances of this embodiment, PRG4 acts as the surface bound receptor that is allowed to interact with endogenous proteins and proteoglycans within the tear film to establish a sacrificial mechanism to reduce the friction during eyelid blinks at the ocular surface, prevent protein adsorption at the ocular surface, and reduce dry spots caused by tear film instability.

In another embodiment of the current invention, PRG4 is applied topically and associates or binds to the ocular surface, in combination with one or more of hyaluronic acid and phospholipid constructs. In certain instances of this embodiment, PRG4 acts as the surface bound receptor that interacts with the exogenously supplied hyaluronic acid and/or phospholipids to establish the sacrificial mechanism to reduce the friction during eyelid blinks at the ocular surface, prevent protein adsorption at the ocular surface, and reduce dry spots caused by tear film instability. In this embodiment, the hyaluronic acid and phospholipid constructs disassociate from the PRG4 during a shear event. In yet another embodiment, the entire construct detaches during a shear event to prevent the shear stress from reaching the epithelium.

In yet another embodiment, functional fragments, multimers (e.g., dimers, trimers, tetramers, etc.), homologs or orthologs of PRG4 act as the surface receptor and/or gel forming constructs in the sacrificial mechanism. Functional fragments and homologs of PRG4 include those with a fewer repeats within the central mucin-like KEPAPTT-repeat (SEQ ID NO: 4) domain, glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the ophthalmic lubricating effect of human PRG4, as measured qualitatively, mechanically, optically, electrically, or by biochemical assay.

As used herein, the term "PRG4", "PRG4 protein" or "proteoglycan 4" protein, is used interchangeably with the term "lubricin" protein. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4gene exons that encode the full length PRG4 protein or isoforms' primary structures. The proteoglycan 4 (prg4) gene contains 12 exons. The PRG4 protein used herein comprises an amino acid sequence encoded by prg4gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO:1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology. In certain embodiments, a preferred PRG4 protein has an average molar mass of between 50 kDa and 400 kDa, comprising one or more biological active portions of the PRG4 protein, or functional fragments, such as a lubricating fragment, or a homolog thereof.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased ocular boundary lubrication.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433, 142; 7,030,223; 7,361,738 to Turner et al., and U.S. Pat. Nos. 6,743,774 and 6,960,562 to Jay et al. U.S. Publication No. 20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 95%, 96%, 97%, 98%, 99%, or more homology, to a wild type PRG4 protein encoding nucleic acid.

As used herein, the term 'cDNAs" includes DNA that is complementary to mRNA molecules present in a cell or organism mRNA that can be convened into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1).

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO:1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10×Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1× SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10×Denhart's solution, 6×SSC, 0.5% SDS and 100 mg/ml denatured salmon sperm DNA. Blots are washed sequentially at 65° C. for 30 minutes each time in 3×SSC/ 0.1% SDS, followed by 1×SSC/0.1% SDS, and finally 0.1× SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

In certain embodiments, the present invention provides a pharmaceutical composition suitable for topical administration to an ocular surface of an individual in need a pharmaceutically effective concentration of PRG4 protein suspended in an ophthalmically acceptable balanced salt solution, and in combination with one or more ophthalmically acceptable agents. The ophthalmically acceptable agents can be selected from the group consisting of an ophthalmically acceptable demulcent, excipient, astringent, vasoconstrictor, and emollient. As used herein, the term "effective concentration or amount" or "therapeutically effective concentration or amount" is intended to mean a nontoxic but sufficient concentration or amount of a PRG4 protein or other therapeutic agents to provide the desired therapeutic effects. The concentration or amount that is effective will vary from subject to subject, depending on the age and general condition of the individual, the particular agents, and the like. Thus, it is not always possible to specify an exact effective concentration or amount. However, an appropriate effective concentration or amount in any individual case may be determined by one of ordinary skill in the art using routine experimentation. Furthermore, the exact effective concentration or amount of a PRG4 protein and other therapeutic agent incorporated into a composition or dosage form of the present invention is not critical, so long as the concentration is within a range sufficient to permit ready application of the solution or formulation so as to deliver an amount of the PRG4 protein and other active agents that is within a therapeutically effective range.

In certain embodiments, pharmaceutical compositions described herein include any composition that provides an ophthalmic benefit. In certain embodiments, such compositions include compositions to be administered to the eye, such as an eye drop. In further or additional embodiments, such compositions include compositions for the care (e.g., treatment) of ophthalmic devices. In certain instances, the care (e.g., treatment) of an ophthalmic device with a composition described herein provides ophthalmic benefit by, e.g., providing a less ophthalmically irritating device.

In some embodiments, compositions (e.g., solutions) described herein are useful in association with ophthalmic devices, such as contact lenses or any other device that may be inserted into the eye. For example, in various embodiments, such compositions (e.g., solutions) are useful for or are used for treating, disinfecting, cleaning, soaking, conditioning, wetting, and/or storing a contact lens. In certain embodiments, for the care of a contact lens with a composition provided herein provides substantial comfort and acceptability benefits to the users of a contact lens or other ophthalmic device treated with a composition or solution described herein.

Exemplary contact lens compositions can be found in the art, for example in the WO 04/058930, which is incorporated herein for additional excipients disclosed therein. In certain instances, contact lens compositions (e.g., disinfectants) other than those described herein may have deleterious effects on the tear film. Any discontinuity and instability of this tear film over the cornea may lead to ocular surface disorder, dry eye and/or hyperosmolarity. Ocular surface disorders are assessed by different clinical tests including breakup time test, the Schirmer test, fluorescein and rose bengal staining, osmolarity and biomicroscopy (Stulting et al. in Leibowitz, Corneal Disorders, Clinical Diagnosis and Management, W. B. Saunders, Philadelphia, Pa., pp. 445-468, 1984).

Provided in certain embodiments herein are compositions (e.g., solutions) and methods which allow the proper care or treatment (e.g., disinfecting and storage) of a contact lens products. In specific embodiments, these compositions and methods are suitable for use with a ophthalmic device (e.g., contact lens product) without having an adverse effect on the ocular surface and tear film once the lens is reintroduced. In certain embodiment, provided herein are composition containing PRG4 or Lubricin for disinfecting, cleaning, soaking, conditioning, wetting, storing or rinsing contact lenses.

In some embodiments, provided herein is a contact lens care composition comprising PRG4. In certain embodiments, the PRG4 is present in any amount as described herein, e.g., in an amount effective for providing ophthalmic benefit to a user of the contact lens.

In some embodiments, the contact lens care composition is a composition for cleaning and/or disinfecting an ophthalmic device, such as contact lens. In further or alternative embodiments, the contact lens care composition is a composition for storing the ophthalmic device. In certain embodiments, provided herein is am ophthalmic system or kit comprising an ophthalmic device and any composition described herein. In specific embodiments, the system comprises a sealed container (e.g., blister pack or contact lens case with a removable, such as screw-on, top), a contact lens, and a composition described herein (e.g., a composition comprising an effective amount of PRG4 suspended in an ophthalmically acceptable balanced salt solution).

The composition (e.g., a composition for the care of an ophthalmic device) may also comprise a surfactant in an amount effective in cleaning a contact lens. Examples of surfactants are poloxamines, poloxamers, alkyl ethoxylates, alkyl phenyl ethoxylates or other non-ionic, anionic and dipolar ionic surfactants known in the art.

In some embodiments, a composition described herein (e.g., a composition for the care of an ophthalmic device) comprises a viscosity increasing-component, preferably selected from the group of cellulose derivatives, polyols, polyethylene oxide (PEO) containing polymers, polyvinyl alcohol and polyvinyl pyrrolidone. Cellulose derivatives are for example cationic cellulose polymers, hydroxypropyl methylcellulose, hydroxyethylcellulose and methylcellulose. An example of a polyol is polyethylene glycol.

In certain embodiments, a composition provided herein additionally comprises a chelating component, preferably ethylenediaminetetraacetic acid, alkali metal salts of ethylenediaminetetraacetic acid or mixtures thereof.

In some embodiments, a composition provided herein (e.g., a composition for the care of an ophthalmic device) additionally comprises a protease. Proteases (enzymatic cleaners) are especially useful for contact lens wearers susceptible to high levels of protein deposits.

In certain embodiments, a composition provided herein (e.g., a composition for the care of an ophthalmic device) additionally comprises disinfectants. Suitable disinfectants are those generally employed in ophthalmic applications and include, but are not limited to, quaternary ammonium salts used in ophthalmic applications such as poly[dimethylimino-2-butene-1,4-diyl]chloride, alpha-[4-tris(2-hydroxyethyl) ammonium]-dichloride, benzalkonium halides, and biguanides, such as salts of alexidine, alexidine-free base, salts of chlorhexidine, hexamethylene biguanides and their polymers, and salts thereof, antimicrobial polypeptides, chlorine dioxide precursors, and the like and mixtures thereof. Generally, the hexamethylene biguanide polymers (PHMB), also referred to as polyaminopropyl biguanide (PAPB), is preferred.

In certain embodiments, the effective concentration of PRG4 protein is in a range of 10-10,000 µg/mL, preferably 50-5,00 mg/mL, and more preferably 100-300 mg/mL. As used herein, the ophthalmically acceptable agents comprising the ophthalmically acceptable demulcents, excipients, astringents, vasoconstrictors, and emollients that are fully defined in the Code of Federal Regulations 21CFR349.

As used herein, the term "topical administration" is used in its conventional sense to mean delivery of the composition comprising the PRG4 protein and one or more ophthalmically acceptable agents to the eye. In general, topical administration is achieved through a liquid formulation for eye drops or lavage and provides a local effect.

In certain embodiments, any composition described herein comprise or the aforementioned ophthalmically acceptable agents are or can be combined with one or more of carboxymethylcellulose sodium (e.g., about 0.2 to about 2.5% w/v), hydroxyethyl cellulose (e.g., about 0.2 to about 2.5% w/v), hypromellose (e.g., about 0.2 to about 2.5% w/v), methylcellulose (e.g., about 0.2 to about 2.5% w/v), dextran 70 (e.g., about 0.1% w/v), gelatin (e.g., about 0.01% w/v), glycerin (e.g., about 0.2 to about 1% w/v), polyethylene glycol 300 (e.g., about 0.2 to about 1% w/v), polyethylene glycol 400 (e.g., about 0.2 to about 1% w/v), polysorbate 80 (e.g., about 0.2 to about 1% w/v), propylene glycol (e.g., about 0.2 to about 1% w/v), polyvinyl alcohol (e.g., about 0.1 to about 4% w/v), povidone (e.g., about 0.1 to about 2% w/v), zinc sulfate (e.g., about 0.25% w/v), anhydrous lanolin (e.g., about 1 to about 10% w/v), lanolin (e.g., about 1 to about 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v), ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v). In certain instances, percent amounts utilized herein are percent amounts by weight.

In further embodiments, the composition of the present invention comprising a PRG4 protein in combination with one or more ophthalmically acceptable agents discussed above further comprises an effective concentration of hyaluronic acid or sodium hyaluronate in the range of 10-100,000 µg/mL, preferably 500-5,000 mg/mL. Furthermore, the composition of the present invention further comprises one or more surface active phospholipids in the range of 10-10,000 µg/mL, such surface active phospholipids include, but are not limited to, L-α-dipalmitoylphosphatidylcholine (DPPC), phosphatidylcholine (PC), phosphatidylethanolamine (PE) and sphingomyelin (Sp), or other neutral and polar lipids.

The composition of the present invention may further comprise one or more ophthalmically acceptable carriers or vehicles comprising any acceptable materials, and/or any one or more additives known in the art. As used herein, the term "carriers" or "vehicle" refer to carrier materials suitable for topical drug administration. Carriers and vehicles useful herein include any such materials known in the art, which are nontoxic and do not interact with other components of the composition in a deleterious manner. Various additives, known to those skilled in the art, may be included in the composition. For example, solvents, including relatively small amounts of alcohol, may be used to solubilize certain drug substances. Other optional additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. Permeation enhancers and/or irritation-mitigating additives may also be included in the composition of the present invention.

In certain embodiments, the composition of the present invention is prepared in a ophthalmically acceptable carrier, such as a phosphate buffered saline or an osmotically balanced salt solution of tear electrolytes, including one or more of sodium chloride in about 44% to about 54% mole fraction, potassium chloride in about 8% to about 14% mole fraction, sodium bicarbonate in about 8% to about 18% mole fraction, potassium bicarbonate in about 0% to about 4% mole fraction, calcium chloride in about 0% to about 4% mole fraction, magnesium chloride in about 0% to about 4% mole fraction, trisodium citrate in about 0% to about 4% mole fraction, and hydrochloric acid in about 0% to about 20% mole fraction or sodium hydroxide in about 0% to about 20% mole fraction. In certain embodiments, the ophthalmically acceptable carrier can be formulated to generate an aqueous electrolyte solution in about 150-200 mM range. Other suitable formulations, such as ointments, creams, gels, pastes, and the like, suitable for topical administration, are also contemplated in the present invention. In certain embodiments, electrolytes provide proper osmotic balance when combined with PRG4 to make a solution ophthalmically acceptable.

The present invention further provides a method for treating decreased or undesired ocular boundary lubrication, symptoms associated therewith, or a condition that is associated with or causes a deficiency in ocular lubrication, in an individual in need thereof, comprising topically administering to the ocular surface of the individual in need a composition comprising an effective amount of PRG4 protein. In one embodiment, the method of the present invention comprises topically administering a composition comprising an effective amount of the PRG4 protein that is suspended in a phosphate buffered saline solution or an ophthalmically acceptable balanced salt solution comprising one or more electrolytes. In yet other embodiment, the method of the present invention comprising topically administering a composition comprising the PRG4 protein formulated in an ophthalmically acceptable formulation comprising one or more additional ophthalmically acceptable agent as discussed above.

As used herein, the term "treating or treatment" refers to reduction in severity and/or frequency of symptoms, elimination of symptoms and/or underlying cause, prevention of the occurrence of symptoms and/or their underlying cause, and improvement or remediation of damage. The term "treating or treatment" also encompasses both prevention of a disorder in a predisposed individual and treatment of the disorder in a clinically symptomatic individual. "Treatment" or "care" of an ophthalmic device (e.g., contact lens) includes, e.g., disinfecting, cleaning, soaking, conditioning, wetting, storing, rinsing, or the like of an ophthalmic device.

In certain embodiments, the decreased ocular boundary lubrication is caused by increased evaporative tear loss or unstable tear film in the ocular boundary loop. Such decreased or undesired ocular boundary lubrication is associated with aqueous or evaporative dry eye disease, Sjogren's syndrome, keratoconjunctivitis sicca (KCS), androgen deficiency, meibomian gland disease, estrogen replacement therapy, contact lens wear, refractive surgery, allergy, reduced tear film breakup time, compromised tear film, ocular surface disorders, increased protease levels in the tear film and at the ocular surface, chronic inflammation, hyperosmolarity, and aging. As discussed above, the increased shear stress leads to tear film instability, evaporative tear loss, hyperosmolarity, changes in swelling pressure and a feedback elevation in shear stress. Increased shear stress also promotes inflammation, androgen deficiency and decreased expression of proteoglycans. Over time, increased shear stress and its sequelae leads to a loss of boundary lubrication at the ocular surface. Accordingly, the present invention provides a method for reducing shear stress by replenishing and enriching the expression of proteoglycans, such as PRG4 protein at the ocular surface, so as to prevent or increase ocular boundary lubrication.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of the preferred embodiments thereof and from the claims. These and many other variations and embodiments of the invention will be apparent to one of skill in the art upon a review of the appende description and examples.

EXAMPLES

Example 1

PRG4 mRNA Expression in Human Corneal and Conjunctival Epithelial Cells

Human corneal epithelial cells were isolated from the corneoscleral rims of male and female donors. Cells were processed either directly (n=8), or first cultured in phenol red-free keratinocyte serum free media (n=2). Bulbar conjunctivae (n=2), conjunctival impression cytology samples (n=9), immortalized human conjunctival epithelial cells after culture (n=1), NOD mouse lacrimal glands (n=5 adult mice/sex, 10 glands/sample), and BALB/c mouse meibomian glands (n=7 adult mice/sex, glands from 28 lids/sample) were obtained during surgical procedures. These samples were processed for the analysis of PRG4 mRNA by using primarily RT-PCR (n=18 human, all mouse) and Affymetrix GeneChips (n=4 human corneas). The PRG4 primers for PCR spanned over 1 kbp of intron sequences, in order to suppress amplification of contaminating chromosomal DNA (Table 1). Amplified samples were screened for the presence of PRG4 products by using agarose gel electrophoresis and an Agilent 2100 Bioanalyzer. To confirm the identity of amplicons, PCR products from cornea samples (n=2), conjunctival epithelial cells (n=1) and a human liver standard (n=1) were sequenced with a 3100 Genetic Analyzer at the Massachusetts Eye and Ear Infirmary DNA Sequencing Center for Vision Research (Boston, Mass.) and resulting data were analyzed with BLASTn searches of GenBank databases.

TABLE 1

Oligonucleotide primers designed for RT-PCR analysis of PRG4 mRNA

| Species | Orientation (5'-3') | Nucleotide sequence | Exons | Amplicon Size (bp) |
|---|---|---|---|---|
| Human | Sense | GATGCAGGGTACCCCAAA (SEQ ID NO: 2) | 9-12 | 526 |
|  | Anti-sense | CAGACTTTGGATAAGGTCTGCC (SEQ ID NO: 3) |  |  |

It was demonstrated that PRG4 mRNA is present in all human corneal and conjunctival epithelial cell and impression cytology samples. The identity of PRG4 PCR products was confirmed by DNA sequence analysis (Table 2). The results show that PRG4 is transcribed in human corneal and conjunctival epithelial cells.

TABLE 2

Identification of amplicon sequences from human cornea, conjunctival and liver samples

| Sequencing Direction | Aligned Base Pairs To Human PRG4 | Total Base Pairs from Amplicon | BLASTn Search Identity |
|---|---|---|---|
| Human Liver Standard | | | |
| A Forward | 495 | 500 | Human PRG4 |
| A Reverse | 488 | 491 | Human PRG4 |
| B Forward | 496 | 499 | Human PRG4 |
| B Reverse | 498 | 500 | Human PRG4 |
| Human Cornea (24 year old female) | | | |
| A Forward | 497 | 499 | Human PRG4 |
| A Reverse | 490 | 492 | Human PRG4 |
| B Forward | 500 | 504 | Human PRG4 |
| B Reverse | 498 | 501 | Human PRG4 |
| Human Cornea (51 year old female) | | | |
| A Forward | 498 | 499 | Human PRG4 |
| A Reverse | 474 | 489 | Human PRG4 |
| B Forward | 496 | 498 | Human PRG4 |
| B Reverse | 490 | 491 | Human PRG4 |
| Human Conjunctival Epithelial Cells | | | |
| A Forward | 496 | 499 | Human PRG4 |
| A Reverse | 490 | 492 | Human PRG4 |
| B Forward | 495 | 499 | Human PRG4 |
| B Reverse | 474 | 491 | Human PRG4 |

Two different samples (A & B) of each preparation were sequenced in forward and reverse directions.
The human cornea samples were epithelial cells from the corneoscleral rims of female donors. The gene accession number for human PRG4 is NM_005807.

Example 2

Reduction of Friction In Vitro With the Addition of PRG4 (Lubricin)

An in vitro friction test with clinically relevant interfaces, such as an ocular surface-eyelid and ocular surface-contact lens interface is described below. Clinically relevant methods capable of quantitatively assessing the lubricating ability of artificial tears are currently lacking. Friction tests with synthetic (e.g. latex and glass) or non-ocular 'native' surfaces (e.g. umbilical cord vein segments) may facilitate some, but likely not all of the molecular interactions that occur during articulation/blinking. Indeed, the relevance of data obtained with non-tissue interfaces is unclear.

An annulus-on-disk rotational test configuration has been shown to be ideal for studying boundary lubrication at an articular cartilage-cartilage interface. A boundary mode of lubrication is indicated by kinetic friction being invariant with factors that influence formation of a fluid film, including sliding velocity and axial load. This is because surface-to-surface contact is occurring, and surface bound molecules contribute to lubrication (by decreasing friction and wear). Boundary lubrication has been discovered to be a critical and operative mechanism at the ocular surface, like it is at the articular cartilage surface. Therefore, the in vitro friction test previously developed and characterized to study boundary lubrication at an articular cartilage-cartilage interface was modified for the study of ocular surface-eye lid and ocular surface-contact lens interfaces.

To determine the test conditions in which boundary lubrication is dominant at the ocular surface-eyelid and ocular surface-contact lens interfaces, the dependence of frictional properties on axial load and sliding velocity was examined. Normal fresh human ocular surfaces (resected corneas with ~3 mm of sclera) were obtained from the Lions Eye Bank of Alberta. The resected corneas were stored in Optisol-GS at 4° C. and used within 2 weeks. Eyelids (age 60-80 years old) were obtained from the University of Calgary Body Donation Program within 1-3 days after death and used immediately or stored at −20° C. in saline for at most 2 weeks until use. Comparative lubricants consisted of Lens Plus Sterile Saline Solution (Advanced Medical Optics) as a negative control; Systane® Lubricant Eye Drops (Alcon Laboratories), Refresh Tears Lubricant Eye Drops (Allergan), Aquify® Long Lasting Comfort Drops (CIBA Vision) and Blink® Tears Lubricant Eye Drops (Advanced Medical Optics) as test lubricants.

Figure 6:
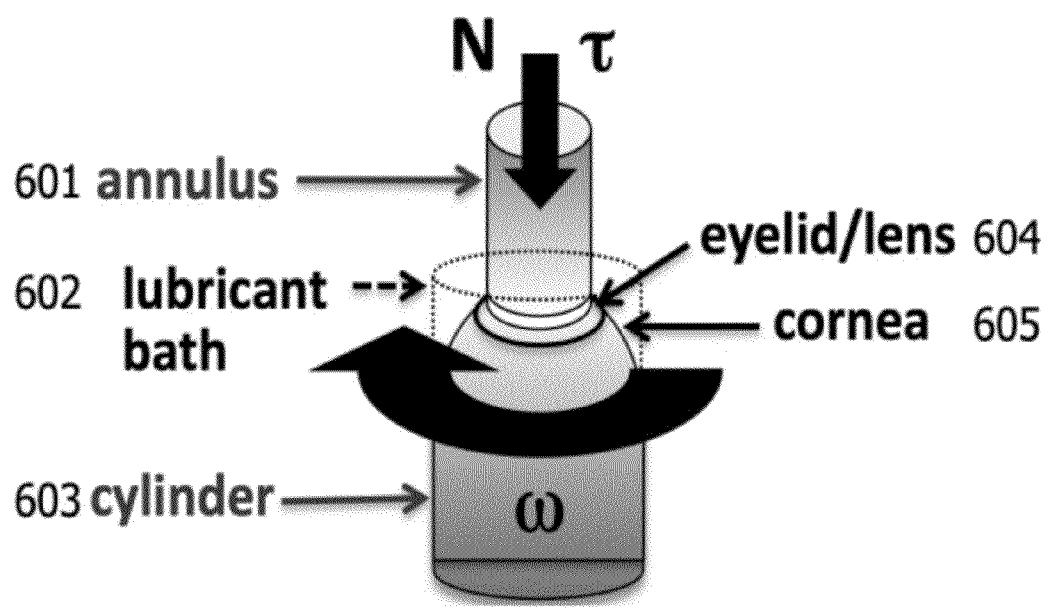
FIG. 6 illustrates a friction test schematic. The corneal ocular surface (605) was fastened to the spherical end of an inert non-permeable semi-rigid rubber plug cylinder (603) (radius r=6 mm) The plug cylinder (603) was attached to the rotational actuator of the mechanical testing machine (Bose ELF 3200) forming the bottom articular surface. An annulus (601) (outer radius=3.2 mm, inner radius=1.5 mm) was punched from the eyelid (604). The annulus (601) was attached to the linear actuator coupled with an axial load (N) and torsion (τ) load cells, forming the upper articulating surface. Lubricant bath (602) was formed by securing an inert tube around the plug cylinder (603). ω is the angular frequency.

The friction test schematic is shown in FIG. 6. The corneal ocular surface (605) was fastened to the spherical end of an inert non-permeable semi-rigid rubber plug cylinder (603) (radius r=6 mm) by applying super glue to the sclera. This plug cylinder (603) was attached to the rotational actuator of the mechanical testing machine (BoseELF 3200) thus forming the bottom articular surface. An annulus (601) (outer radius=3.2 mm, inner radius=1.5 mm) was punched from the eyelid (604), and was attached to the linear actuator coupled with an axial load (N) and torsion (t) load cell, thus forming the upper articulating surface. Lubricant bath 602 was formed by securing an inert tube around the plug cylinder (603).

Samples were first tested in saline, then in one of the three (3) test lubricants. The lubricant bath was filled with ~0.3 ml, and the articulating surfaces allowed to equilibrate with the lubricant. The sample surfaces were slowly (0.05 mm/s) brought into contact and compressed until the spherical plug flattened out and the entire annular eyelid surface was in contact with the cornea (605). The resulting normal stress (calculated from axial load as, in units of MPa, as $N/(\pi [r^2_{outer} - r^2_{inner}])$ can be varied by using different stiffness rubber plugs to mimic physiological stresses ~5kPa. The test sequence was initiated by preconditioning the sample by rotating +4 revolutions (rev) and reset with −4 revolutions at a physiologically relevant effective linear sliding velocity, veff=30 mm/s (where veff=ωReff, ω is the angular frequency, and Reff=2.4 mm is the effective radius calculated by integrating the shear stress distribution over the annular contact area). Samples were then tested by rotating +4 revolutions, immediately followed by −4 reset revolutions at veff=30, 10, 1, 0.3 and then 30 mm/s, with a dwell time of 12 second between each revolution. The test sequence was then be repeated in the opposite direction of rotation.

To evaluate the lubrication properties of the ocular surface, two friction coefficients ($\mu$) of the form $\mu=\tau/(R_{eff}N)$ where is torque, $R_{eff}$ is effective radius, and N is axial load, described above. A static friction coefficient, which reflects the resistance to the onset of motion, $\mu_{static}$ was calculated as the peak value of $\mu$, just after (within ~10°) the start of rotation. An average kinetic friction coefficient, which reflects the resistance to steady state motion, $<\mu_{kinetic}>$ was calculated from $\mu$ averaged during the third and fourth complete test revolution. Both $\mu_{static}$ and $<\mu_{kinetic}>$ were averaged for the + and − revolutions in each test to account for potential directional effects on i measurements. Data was collected at a frequency of 20 Hz.

Figure 7:
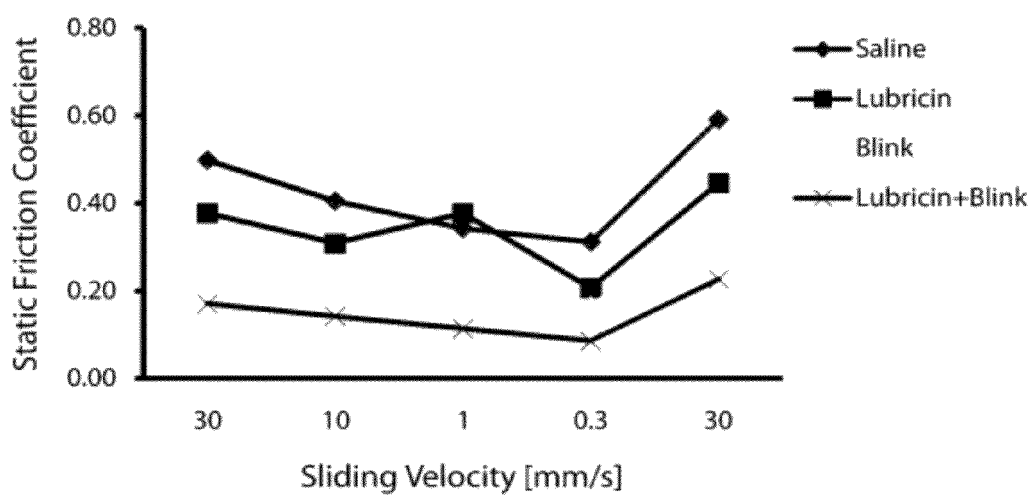
FIG. 7 illustrates the reduction of in vitro lid/cornea kinetic friction with addition of PRG4 protein (lubricin).
Figure 7:
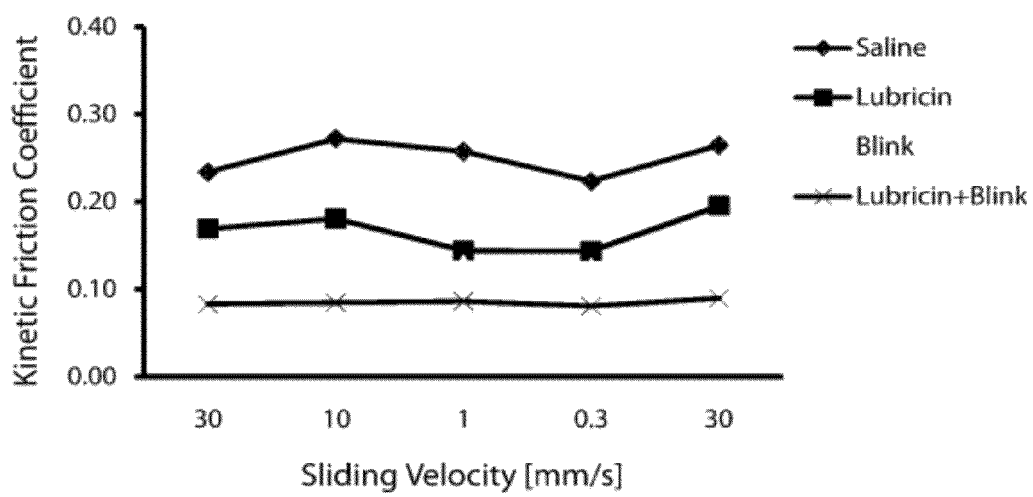

The results of lubricin (PRG4) added to the corneal surface at a concentration in the range of 100-300 ug/mL are shown in FIG. 7. Lubricin had a friction lowering effect at the eyelid interface, both in terms of kinetic and static friction, at all velocities. At a concentration 1/10th of that of physiological hyaluronic acid, lubricin was similar to Blink® Tears Lubricant Eye Drops, which contains hyaluronic acid. In combination, the two lubricants are better than either alone.

Figure 8:
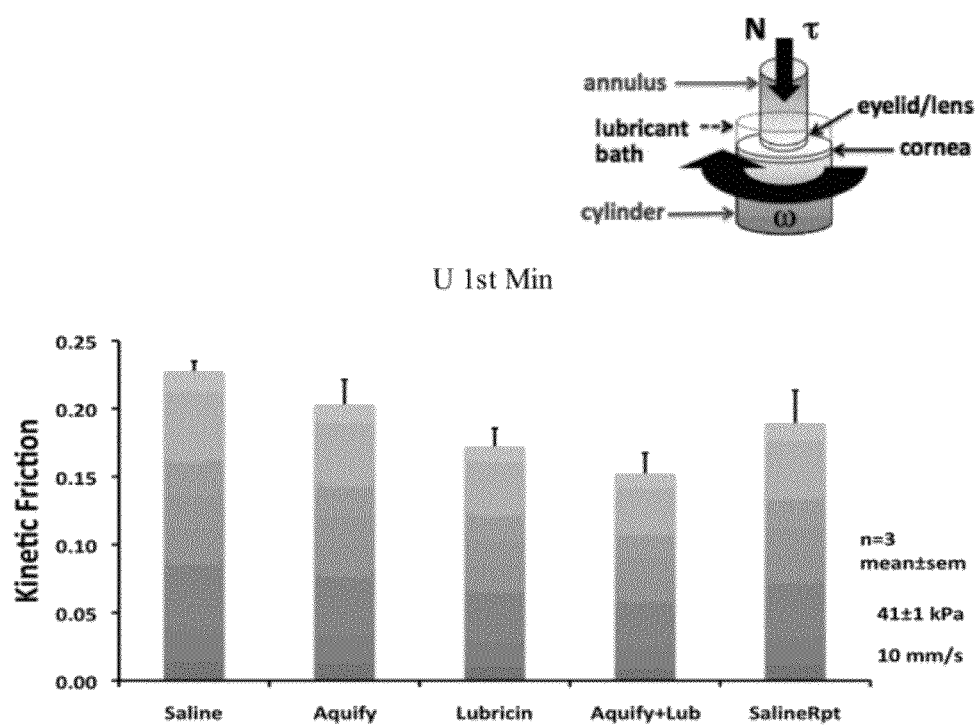
FIG. 8 illustrates the reduction of in vitro lid/cornea kinetic friction measured 1 minute after the addition of PRG4 protein (lubricin).

FIG. 8 demonstrates the reduction of in vitro cornea/lid kinetic friction measured during the first minute after the addition of lubricin, as compared to Aquify® eye drops. Lubricants were thoroughly washed from the ocular surface using saline between tests. A synergistic effect (reduced $\mu_{kinetic}$ over either alone) was evident when Aquify® (with hyaluronic acid) was combined with lubricin. The saline repeat was lower than the original saline control. This showed a retention of lubricin's effect even after washing with saline, suggesting that the molecules were binding to the ocular surface, and that lubricin demonstrated superior retention time as compared to sodium hyaluronate alone.

Figure 9:
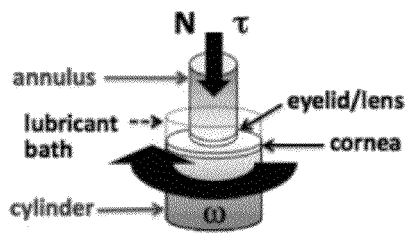
FIG. 9 illustrates the reduction of in vitro lid/cornea kinetic friction measured 5 minutes after the addition of PRG4 protein (lubricin).
Figure 9:
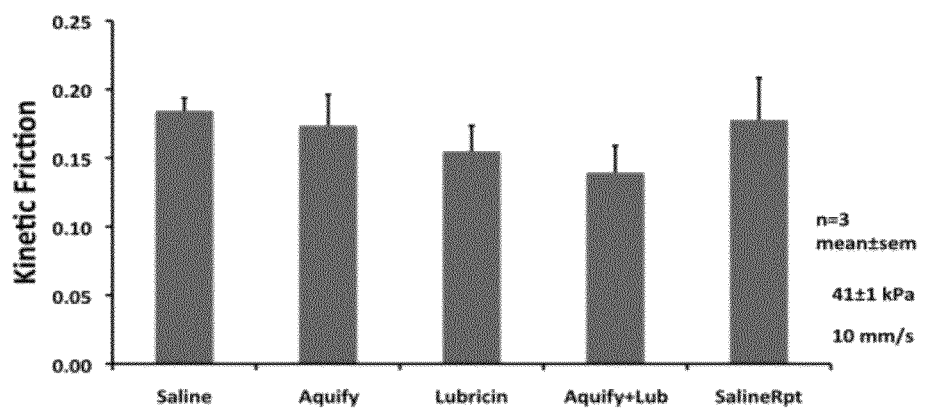

FIG. 9 demonstrates the reduction of in vitro cornea/lid kinetic friction measured during the 5th minute after the addition of lubricin, as compared to Aquify® eye drops. A synergistic effect (reduced $\mu_{kinetic}$ over either alone) was evident when Aquify® (with hyaluronic acid) was combined with lubricin. The friction coefficient of Aquify® had returned to statistical equivalence to saline after 5 minutes, whereas lubricin remains lower, as did the combination of lubricin and hyaluronic acid.

Figure 10:
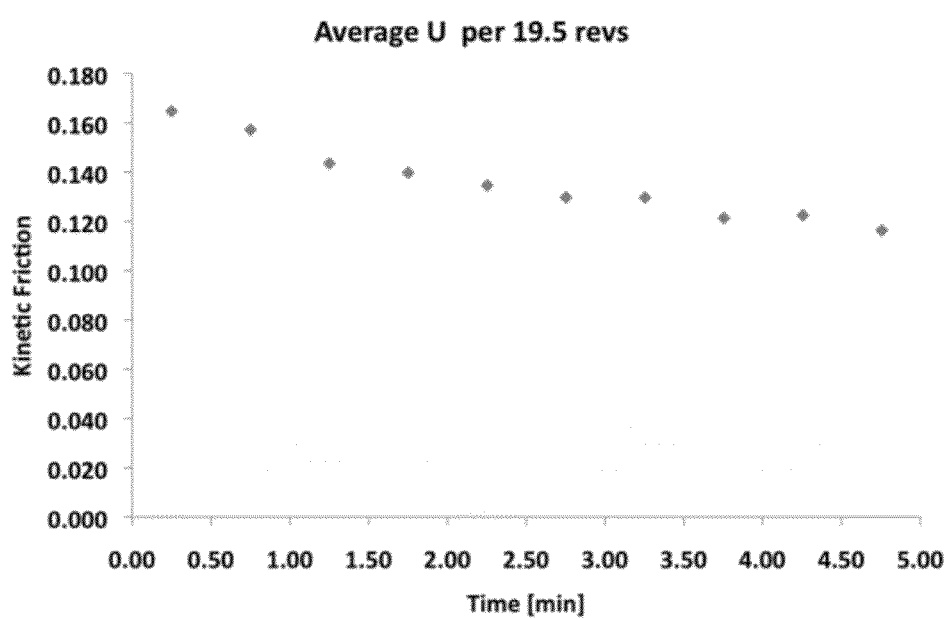
FIG. 10 illustrates the reduction of in vitro lid/cornea kinetic friction over time, following addition of PRG4 protein (lubricin).

FIG. 10 shows the reduction of kinetic friction coefficient over time, following addition of lubricin. Again, the continual reduction suggested binding to the ocular surface.

Example 3

Treatment of Deficient Ocular Boundary Lubrication in Vivo

A patient complaining of ocular surface irritation is examined for ocular lubrication or conditions associated with a deficiency in ocular lubrication by measuring symptoms greater than 2 positive responses on the McMonnies questionnaire, greater than a score of 5 on the Ocular Surface Disease Index (OSDI), or through evidence of some symptoms on the Visual Analog Scale, in combination with objective signs including one or more of a reduced tear film breakup time (less than ≈10 seconds), inferior lateral tear meniscus osmolarity greater than 308 mOsms/L, low Schirmer strip value (less than ≈10 mm), sodium fluorescein corneal or conjunctival staining (scores>0 with multiple macropunctates), significant debris resulting from impression cytology, meibomian gland dysfunction however determined, a decrease in the rate of post-blink displacement of a contact lens, a change in the spatiotemporal transfer function of a contact lens following application of a series of pressure impulses, a decrease in the rate of post-blink interferometric tear film relaxation, an increase in the concentration of proinflammatory cytokines, a reduced concentration of lactoferrin or lysozyme, or an increase in the rate of post-blink point spread function decoherence.

The patient administers 1 to 2 drops on the surface of each eye a solution containing 200 µg/mL PGR4 protein suspended in an ophthalmically acceptable balanced salt solution. The patient is instructed to close their eyes for 10 seconds.

Follow-up visits may track a reduction in inferior lateral tear osmolarity, increased tear film breakup time, or the other aforementioned signs. In particular if the tear film osmolarity is reduced from an abnormal value (perhaps 330 mOsms/L) to a more normal value (perhaps 304 mOsms/L), the therapeutic modulation and replenishment of the ocular surface lubrication would be deemed successful.

References

1. G. D. Jay, Curr Opin Orthop 15, 355 (2004).
2. D. A. Swann, R. B. Hendren, E. L. Radin, S. L. Sotman, E. A. Duda, Arthritis Rheum 24, 22 (1981).
3. G. D. Jay, D. E. Britt, D. -J. Cha, J Rheumatol 27, 594 (2000).
4. G. D. Jay, Connect Tissue Res 28, 71 (1992).
5. G. D. Jay, B. P. Lane, L. Sokoloff, Connect Tissue Res 28, 245 (1992).
6. G. D. Jay, B. -S. Hong, Connect Tissue Res 28, 89 (1992).
7. G. D. Jay, K. Haberstroh, C. -J. Cha, J Biomed Mater Res 40, 414 (1998).
8. G. D. Jay, D. A. Harris, C. -J. Cha, Glycoconj J 18, 807 (2001).
9. G. D. Jay, U. Tantravahi, D. E. Britt, H. J. Barrach, C. J. Cha, J Orthop Res 19, 677 (2001).
10. C. R. Flannery et al., Biochem Biophys Res Commun 254, 535 (1999).
11. B. L. Schumacher, J. A. Block, T. M. Schmid, M. B. Aydelotte, K. E. Kuettner, Arch Biochem Biophys 311, 144 (1994).
12. T. Schmid, V. Soloveychik, K. Kuettner, B. Schumacher, Trans Orthop Res Soc 26, 178 (2001).
13. S. G. Rees et al., Matrix Biology 21, 593 (2002).
14. Schumacher B L, Schmidt T A, Voegtline M S, Chen A C, Sah R L. Proteoglycan 4 (PRG4) synthesis and immunolocalization in bovine meniscus. J Orthop Res. 2005 May; 23(3):562-8.
15. J. Marcelino et al., Nat Genet 23, 319 (1999).
16. D. K. Rhee et al., J Clin Invest 115, 622 (2005).
17. B. Xia, J. A. Royall, G. Damera, G. P. Sachdev, R. D. Cummings, Glycobiology 15, 747 (August 2005).
18. K. Godl et al., J Biol Chem 277, 47248 (Dec. 6, 2002).
19. D. A. Swann, S. Sotman, M. Dixon, C. Brooks, Biochem J 161, 473 (1977).
20. Schmidt T A, Plaas A H, Sandy J D. Disulfide-bonded multimers of proteoglycan 4 (PRG4) are present in normal synovial fluids. Biochim Biophys Acta. 2009 Mar. 27.
21. K. A. Elsaid, G. D. Jay, M. L. Warman, D. K. Rhee, C. 0. Chichester, Arthritis Rheum 52, 1746 (June 2005).
22. G. D. Jay et al., J Rheumatol 31, 557 (2004).
23. A. M. Malfait et al., J Rheumatol 21, 314 (February 1994).
24. T. A. Schmidt et al., in Physical Regulation of Skeletal Repair R. K. Aaron, M. E. Bolander, Eds. (American Academy of Orthopaedic Surgeons, Chicago, 2005) pp. 151-162.
25. Nugent-Derfus G E, Chan A H, Schumacher B L, Sah R L. PRG4 exchange between the articular cartilage surface and synovial fluid. J Orthop Res. 2007 October; 25(10):1269-76.
26. T. A. Schmidt, B. L. Schumacher, G. E. Nugent, N. S. Gastelum, R. L. Sah, Trans Orthop Res Soc 30, 900 (2005).
27. Nugent G E, Aneloski N M, Schmidt T A, Schumacher B L, Voegtline M S, Sah R L. Dynamic shear stimulation of bovine cartilage biosynthesis of proteoglycan 4. Arthritis Rheum. 2006 June; 54(6):1888-96.
28. D. K. Rhee et al., J Biol Chem 280, 31325 (2005).
29. T. J. Klein et al., Osteoarthritis Cartilage 11, 595 (2003).
30. K. C. Morrell, W. A. Hodge, D. E. Krebs, R. W. Mann, Proc Natl Acad Sci U S A 102, 14819 (Oct. 11, 2005).
31. E. Meyer, R. M. Overney, K. Dransfeld, T. Gyalog, Nanoscience: Friction and Rheology on the Nanometer Scale (World Scientific Publishing Co. Pte. Ltd, River Edge, N.J., 2002), pp. 373.
32. C. W. McCutchen, Fed Proceedings 25, 1061 (1966).

33. T. Murakami, Y. Sawae, M. Ihara, JSME Int J Series C-Mechanical Systems Machine Elements & Manufacturing 46, 594 (2003).
34. G. Meachim, Ann Rheum Dis 31, 457 (1972).
35. D. Dowson, Proc Inst Mech Eng [H] 215, 335 (2001).
36. G. A. Ateshian, V. C. Mow, in Basic Orthopaedic Biomechanics and Mechano-Biology V. C. Mow, R. Huiskes, Eds. (Lippincott Williams & Wilkins, Philadelphia, 2005) pp. 447-494.
37. F. Guilak, Arthritis Rheum 52, 1632 (June 2005).
38. K. C. Morell, W. A. Hodge, D. E. Krebs, R. W. Mann, Proc Natl Acad Sci U S A 102, 14819 (Oct. 11, 2005).
39. S. A. V. Swanson, in Adult Articular Cartilage M. A. R. Freeman, Ed. (Pitman Medical, Tunbridge Wells, England, 1979) pp. 415-460.
40. Elsaid K A, Jay G D, Chichester C O. Reduced expression and proteolytic susceptibility of lubricin/superficial zone protein may explain early elevation in the coefficient of friction in the joints of rats with antigen-induced arthritis. Arthritis Rheum 2007; 56:108-116.
41. Elsaid K A, Jay G D, Warman M L, Rhee D K, Chichester C O. Association of articular cartilage degradation and loss of boundary-lubricating ability of synovial fluid following injury and inflammatory arthritis. Arthritis Rheum 2005; 52:1746-1755.
42. Cutolo M, Capellino S, Sulli A, Serioli B, Secchi ME, Villaggio B, Straub R H. Estrogens and autoimmune diseases. Ann N Y Acad Sci 2006; 1089:538-547.
43. Cutolo M, Sulli A, Capellino S, Villaggio B, Montagna P, Pizzorni C, Paolino S, Seriolo B, Felli L, Straub R H. Anti-TNF and sex hormones. Ann N Y Acad Sci 2006; 1069:391-400.
44. Schmidt M, Naumann H, Weidler C, Schellenberg M, Anders S, Straub R H. Inflammation and sex hormone metabolism. Ann N Y Acad Sci 2006; 1069:236-246.
45. Rontzsch A, Thoss K, Petrow P K, Henzgen S, Brauer R. Amelioration of murine antigen-induced arthritis by dehydroepiandrosterone (DHEA). Inflamm Res 2004; 53:189-198.
46. Zierhut M, Dana M R, Stern M E, Sullivan D A. Immunology of the Lacrimal Gland and Ocular Tear Film. Trends Immunol 2002; 23:333-335
47. Stern M E, Gao J, Siemasko K F, Beuerman R W, Pflugfelder S C. The role of the lacrimal functional unit in the pathophysiology of dry eye. Exp Eye Res 2004; 78:409-416.
48. Tomlinson A, Khanal S, Ramaesh K, Diaper C, McFadyen A. Tear film osmolarity: determination of a referent for dry eye diagnosis. Invest Ophthalmol Vis Sci 2006; 47:4309-4315.
49. Sullivan D A, Sullivan B D, Evans J E, Schirra F, Yamagami H, Liu M, Richards S M, Suzuki T, Schaumberg D A, Sullivan R M, Dana M R. Androgen deficiency, meibomian gland dysfunction and evaporative dry eye. Ann NY Acad Sci 2002; 966:211-222.
50. Sullivan D A. Tearful relationships? Sex, hormones and aqueous-deficient dry eye. Ocular Surface 2004; 2:92-123.
51. Schaumberg D A, Buring J E, Sullivan D A, Dana M R. Hormone replacement therapy and dry eye syndrome. JAMA 2001; 286:2114-2119.
52. de Souza G A, Godoy L M, Mann M. Identification of 491 proteins in the tear fluid proteome reveals a large number of proteases and protease inhibitors. Genome Biol. 2006; 7:R72. Epub 2006.
53. Schirra F, Suzuki T, Dickinson D P, Townsend D J, Gipson I K, Sullivan D A. Identification of steroidogenic enzyme mRNAs in the human lacrimal gland, meibomian gland, cornea and conjunctiva. Cornea 2006; 25:438-42.
54. Schwarz I M, Hills B A, Br. J. Rheum. 1998; 37:21-26.
55. Jay G D, Hong B S. Connect Tissue Res, 1992; 28(1-2): 89-98.
56. Matnelli F, Argüeso P, Curr Opin Allergy Clin Immuno, 2008; 8(5):477-483.
57. Jones M B. et. al. Mathematical Medicine and Biology 2005; 22, 265.
58. Schumacher B L, Hughes C E, Kuettner K E, Caterson B, Aydelotte M B. Immunodetection and partial cDNA sequence of the proteoglycan, superficial zone protein, synthesized by cells lining synovial joints. J Orthop Res. 1999 January; 17(1):110-20.
59. Schmidt T A, Gastelum N S, Nguyen Q T, Schumacher B L, Sah R L. Boundary lubrication of articular cartilage: role of synovial fluid constituents. Arthritis Rheum. 2007 March; 56(3):882-91.
60. Schmidt TA, Plaas AH, Sandy JD. Disulfide-bonded multimers of proteoglycan 4 (PRG4) are present in normal synovial fluids. Biochim Biophys Acta. 2009 Mar. 27.
61. Sullivan DA. The definition and classification of dry eye disease: report of the Definition and Classification Subcommittee of the International Dry Eye WorkShop (2007). Ocular Surface. 2007 April; 5(2):75-92.

---

What is claimed is:

1. A composition for the care of an ophthalmic contact lens, the composition comprising PRG4 disposed in an ophthalmically acceptable balanced salt solution and a contact lens care agent comprising a surfactant, a protease, a disinfectant, or a combination thereof.

2. The composition of claim 1, comprising one or more surfactants.

3. The composition of claim 1, further comprising one or more viscosity increasing components.

4. The composition of claim 1, further comprising one or more chelating components.

5. The composition of claim 1, comprising one or more proteases.

6. The composition of claim 1, comprising one or more disinfectants.

7. The composition of claim 1, comprising a PRG4 at a concentration of 10-10,000 µg/ml.

8. The composition of claim 1, further comprising an effective concentration of sodium hyaluronate or hyaluronic acid.

9. The composition of claim 8, comprising sodium hyaluronate or hyaluronic acid at a concentration of 10-100,000 µg/ml.

10. The composition of claim 9, comprising sodium hyaluronate or hyaluronic acid at a concentration of 500-5,000 µg/ml.

11. The composition of claim 1, comprising a concentration of surface active phospholipid selected from the group consisting of L-α-dipalmitoylphosphatidylcholine, phosphatidylcholine, phosphatidylethanolamine and sphingomyelin.

12. The composition of claim 11, wherein the surface active phospholipid is present at a concentration of 10-10,000 µg/ml.

13. The composition of claim 1, wherein the ophthalmically acceptable balanced salt solution comprises at least three different electrolytes selected from the group consisting of sodium phosphate, sodium chloride, potassium chloride, sodium bicarbonate, potassium bicarbonate, calcium chloride, magnesium chloride, sodium acetate, sodium citrate, hydrochloric acid, and sodium hydroxide.

14. The composition of claim 1, wherein the PRG4 has an average molar mass of between 50 kDa and 400 kDa.

15. The composition of claim 14, wherein the PRG4 comprises a lubricating fragment, multimer or a homolog thereof.

16. The composition of claim 14, wherein the PRG4 is a recombinant PRG4 protein, or functional fragment thereof.

17. The composition of claim 14, wherein the PRG4 is a purified naturally occurring PRG4 protein.

* * * * *

SEQUENCE LISTING

```
<160> NUMBER OF SEQ ID NOS: 4

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45
```

```
Asn Cys Gln His Tyr Met Glu Cys Cys Pro Asp Phe Lys Arg Val Cys
 50                  55                  60
Thr Ala Glu Leu Ser Cys Lys Gly Arg Cys Phe Glu Ser Phe Glu Arg
 65                  70                  75                  80
Gly Arg Glu Cys Asp Cys Asp Ala Gln Cys Lys Lys Tyr Asp Lys Cys
                 85                  90                  95
Cys Pro Asp Tyr Glu Ser Phe Cys Ala Glu Val His Asn Pro Thr Ser
            100                 105                 110
Pro Pro Ser Ser Lys Lys Ala Pro Pro Ser Gly Ala Ser Gln Thr
        115                 120                 125
Ile Lys Ser Thr Thr Lys Arg Ser Pro Lys Pro Asn Lys Lys
130                 135                 140
Thr Lys Lys Val Ile Glu Ser Glu Glu Ile Thr Glu Glu His Ser Val
145                 150                 155                 160
Ser Glu Asn Gln Glu Ser Ser Ser Ser Ser Ser Ser Ser Ser Ser
                165                 170                 175
Ser Thr Ile Arg Lys Ile Lys Ser Ser Lys Asn Ser Ala Ala Asn Arg
            180                 185                 190
Glu Leu Gln Lys Lys Leu Lys Val Lys Asp Asn Lys Lys Asn Arg Thr
        195                 200                 205
Lys Lys Lys Pro Thr Pro Lys Pro Val Val Asp Glu Ala Gly Ser
210                 215                 220
Gly Leu Asp Asn Gly Asp Phe Lys Val Thr Thr Pro Asp Thr Ser Thr
225                 230                 235                 240
Thr Gln His Asn Lys Val Ser Thr Ser Pro Lys Ile Thr Thr Ala Lys
                245                 250                 255
Pro Ile Asn Pro Arg Pro Ser Leu Pro Pro Asn Ser Asp Thr Ser Lys
            260                 265                 270
Glu Thr Ser Leu Thr Val Asn Lys Glu Thr Thr Val Glu Thr Lys Glu
        275                 280                 285
Thr Thr Thr Thr Asn Lys Gln Thr Ser Thr Asp Gly Lys Glu Lys Thr
290                 295                 300
Thr Ser Ala Lys Glu Thr Gln Ser Ile Glu Lys Thr Ser Ala Lys Asp
305                 310                 315                 320
Leu Ala Pro Thr Ser Lys Val Leu Ala Lys Pro Thr Pro Lys Ala Glu
                325                 330                 335
Thr Thr Thr Lys Gly Pro Ala Leu Thr Thr Pro Lys Glu Pro Thr Pro
            340                 345                 350
Thr Thr Pro Lys Glu Pro Ala Ser Thr Thr Pro Lys Glu Pro Thr Pro
        355                 360                 365
Thr Thr Ile Lys Ser Ala Pro Thr Thr Pro Lys Glu Pro Ala Pro Thr
370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Lys Ser Ala Pro Thr Thr Pro
            420                 425                 430
Lys Glu Pro Ala Pro Thr Thr Pro Lys Lys Pro Ala Pro Thr Thr Pro
        435                 440                 445
Lys Glu Pro Ala Pro Thr Thr Pro Lys Glu Pro Thr Pro Thr Thr Pro
450                 455                 460
Lys Glu Pro Ala Pro Thr Thr Lys Glu Pro Ala Pro Thr Thr Pro Lys
465                 470                 475                 480
```

-continued

```
Glu Pro Ala Pro Thr Ala Pro Lys Lys Pro Ala Pro Thr Pro Lys
                485                 490                 495

Glu Pro Ala Pro Thr Thr Pro Lys Glu Pro Ala Pro Thr Thr Lys
                500                 505                 510

Glu Pro Ser Pro Thr Thr Pro Lys Glu Pro Ala Pro Thr Thr Lys
                515                 520                 525

Ser Ala Pro Thr Thr Thr Lys Glu Pro Ala Pro Thr Thr Lys Ser
    530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
                580                 585                 590

Ala Pro Thr Thr Thr Lys Lys Pro Ala Pro Thr Thr Pro Lys Glu Pro
                595                 600                 605

Ala Pro Thr Thr Pro Lys Glu Thr Ala Pro Thr Thr Pro Lys Lys Leu
                610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
                675                 680                 685

Ala Pro Thr Thr Pro Lys Glu Pro Ala Pro Thr Thr Pro Lys Glu Thr
                690                 695                 700

Ala Pro Thr Thr Pro Lys Gly Thr Ala Pro Thr Thr Leu Lys Glu Pro
                705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
        740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
        770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
                820                 825                 830

Glu Pro Ala Pro Thr Thr Pro Lys Lys Pro Ala Pro Thr Thr Pro Glu
                835                 840                 845

Thr Pro Pro Pro Thr Thr Ser Glu Val Ser Thr Pro Thr Thr Thr Lys
                850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910
```

-continued

```
Thr Thr Ala Lys Asp Lys Thr Thr Glu Arg Asp Leu Arg Thr Thr Pro
    915                 920                 925

Glu Thr Thr Thr Ala Ala Pro Lys Met Thr Lys Glu Thr Ala Thr Thr
930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
                980                 985                 990

Thr Thr Thr Glu Ile Met Asn Lys Pro Glu Glu Thr Ala Lys Pro Lys
                995                 1000                1005

Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035

Thr Met Pro Arg Val Arg Lys Pro Lys Thr Thr Pro Thr Pro Arg
    1040                1045                1050

Lys Met Thr Ser Thr Met Pro Glu Leu Asn Pro Thr Ser Arg Ile
    1055                1060                1065

Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110

Phe Met Pro Glu Val Thr Pro Asp Met Asp Tyr Leu Pro Arg Val
    1115                1120                1125

Pro Asn Gln Gly Ile Ile Ile Asn Pro Met Leu Ser Asp Glu Thr
    1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320
```

```
Arg Leu Ala Tyr Gln Asp Lys Gly Val Leu His Asn Glu Val Lys
    1325                1330                1335

Val Ser Ile Leu Trp Arg Gly Leu Pro Asn Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcagggt accccaaa                                                  18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagactttgg ataaggtctg cc                                             22

<210> SEQ ID NO 4
<211> LENGTH: 7
<212> TYPE: PRT
<213> ORGANISM: Homo sapiens

<400> SEQUENCE: 4

Lys Glu Pro Ala Pro Thr Thr
1               5
```